United States Patent [19]

Schmid

[11] Patent Number: 5,124,107
[45] Date of Patent: Jun. 23, 1992

[54] PROCESS FOR MANUFACTURING A BODY ELECTRODE

[76] Inventor: Walter Schmid, Fuchsweg 9, 7914 Pfaffenhofen/Roth, Fed. Rep. of Germany

[21] Appl. No.: 729,832

[22] Filed: Jul. 11, 1991

Related U.S. Application Data

[63] Continuation of Ser. No. 412,296, Sep. 25, 1989, abandoned.

[30] Foreign Application Priority Data

Feb. 27, 1989 [DE] Fed. Rep. of Germany ....... 3906074

[51] Int. Cl.$^5$ .................. B29C 39/10; B29C 39/12
[52] U.S. Cl. .................. 264/255; 264/271.1; 264/279.1; 264/308; 128/640
[58] Field of Search ........... 264/272.11, 275, 277, 264/278, 271.1, 279, 279.1, 299, 308, 255; 128/640, 641

[56] References Cited

U.S. PATENT DOCUMENTS

| | | | |
|---|---|---|---|
| 3,072,973 | 1/1963 | Barnette | 264/308 |
| 3,170,013 | 2/1965 | Ploetz | 264/255 |
| 3,660,211 | 5/1972 | Brody | 264/308 |
| 4,066,078 | 1/1978 | Berg | 128/418 |
| 4,126,126 | 11/1978 | Bare et al. | 339/176 P |
| 4,213,463 | 7/1980 | Osenkarski | 128/639 |
| 4,233,987 | 11/1980 | Feingold | 128/639 |
| 4,270,543 | 6/1981 | Tabuchi et al. | 128/639 |
| 4,272,471 | 6/1981 | Walker | 264/104 |
| 4,273,135 | 6/1981 | Larimore et al. | 128/640 |
| 4,317,278 | 3/1982 | Carmon et al. | 128/639 |
| 4,368,167 | 10/1983 | Berchielli | 264/104 |
| 4,406,827 | 9/1983 | Carim | 128/639 |
| 4,529,595 | 12/1986 | Ito | 264/104 |
| 4,554,924 | 11/1985 | Engel | 128/640 |
| 4,570,637 | 2/1986 | Gomes et al. | 128/639 |
| 4,583,548 | 4/1986 | Schmid | 128/639 |
| 4,583,548 | 4/1986 | Schmid | 128/639 |
| 4,640,289 | 2/1987 | Craighead | 128/639 |
| 4,692,273 | 9/1987 | Lawrence | 252/500 |
| 4,722,761 | 2/1988 | Cartmell et al. | 128/639 |
| 4,750,976 | 6/1988 | Hupe et al. | 204/15 |
| 4,798,642 | 1/1989 | Craighead et al. | 156/252 |
| 4,852,571 | 8/1989 | Gadsby et al. | 128/640 |
| 4,860,754 | 8/1989 | Sharik et al. | 128/640 |

FOREIGN PATENT DOCUMENTS

| | | |
|---|---|---|
| 0085327 | 8/1983 | European Pat. Off. . |
| 0096330 | 12/1983 | European Pat. Off. . |
| 2459627 | 6/1975 | Fed. Rep. of Germany . |
| 3136366 | 4/1983 | Fed. Rep. of Germany . |
| 8700183 | 4/1987 | Fed. Rep. of Germany . |
| 57-27623 | 2/1982 | Japan . |
| 90/00320 | 2/1990 | PCT Int'l Appl. . |

OTHER PUBLICATIONS

PCT/EP 90/00320, Feb. 26, 1990, Walter Schmid International Serach Report.

*Primary Examiner*—Jay H. Woo
*Assistant Examiner*—Jeremiah F.g330105 Durkin, II
*Attorney, Agent, or Firm*—Venable, Baetjer, Howard & Civiletti

[57] ABSTRACT

A process for manufacturing a body electrode is provided. The body electrode includes one or more galvanically active sensors which are combined with a first layer capable of adhering to the skin on the body contact side of said sensors and a second layer on the side of said sensors opposite the body contact side. The first layer comprises an electrically conductive, adherent, elastic hydrophilic material. The second layer is a covering or supporting layer and comprises an elastic non-adherent material. According to the present invention, the layer adhering to the skin and the covering or supporting layer are cast in a mold during manufacture of the electrode. This process eliminates the problems encountered with the prior art stamping process, especially in stamping the conductive layer which adheres to the skin.

31 Claims, No Drawings

PROCESS FOR MANUFACTURING A BODY ELECTRODE

This application is a continuation of application Ser. No. 07/412/296, filed Sep. 25, 1989, now abandoned.

DESCRIPTION

The invention relates to a process for manufacture of a body electrode

Such electrodes are already known. They are fastened to the skin of a patient to be examined or treated and serve the purpose of transmitting electrical signals from the body to a recording instrument or such signals in the opposite direction from a device into the body. They are used, for example, for recording electrocardiograms, as grounding electrodes in operations, or to mitigate pain through transmission of electrical pulses.

These electrodes comprise essentially one or more generally plate-shaped galvanically active sensors which may have a place of attachment for an electrical conductor leading to a recording device or transmitting electrical pulses from a device into the body. The sensor is connected on its body contact side with a first layer capable of adhering to the skin and consisting of an electrically conductive, adhesive, elastic hydrophilic material or combination of materials. This layer serves the purpose of ensuring firm adhesion of the body electrode to the skin while smoothing out unevennesses of the body to make certain of transmission of electrical signals from the body by way of the sensor to a display unit or of a signal generated in an instrument by way of the sensor into the body. On the side of the sensor facing away from the body there is a non-conducting elastic and non-adhesive second layer which is a covering or supporting layer and which covers the electrode plate and the first layer adhering to the skin (if the first layer is larger than the electrode plate) and is connected to the electrode plate.

Electrodes of this kind have thus far been manufactured by stamping parts of the desired size and shape form a strip of a material which adheres to the skin, a sensor then being applied to these preforms, and finally a covering or supporting sheet of suitable size being applied to the side of the sensor plate facing away from the body and if necessary to the layer adhering to the skin.

Because of the adhesiveness of the strip from which the parts of the first layer adhering to the skin are stamped, the stamping process entails difficulties in that the stamped parts tend to adhere to the stamping tool, so that it is difficult to carry out high-speed continuous stamping.

Hence the task was set for the invention to eliminate the disadvantages described in the foregoing by devising a process for manufacture of body electrodes that can be conducted in a trouble-free and a simple, cost-effective manner. This task is accomplished by the process described and claimed herein.

The process according to the present invention consists of casting the first layer adhering to the skin and the second covering or supporting layer in a mold during manufacture of the electrode. Inasmuch as the problem of adhesion of the parts of the layer adhering to the skin no longer exists with the process claimed for the invention, the process can be conducted continuously, trouble-free, and at a high rate of speed on an industrial scale.

It is expedient that the materials used in the process of the present invention for casting the first layer adhering to the skin and the second covering or supporting layer be in the form of a melt, a solution, or a cross-linkable or hardenable preliminary stage.

The materials used for casting in the instant process preferably comprise natural and/or synthetic materials, especially polymers, with particular preference to be given to elastomeric polymers.

Suitable natural materials are, for example, collagens or varieties of natural rubber. Synthetic materials are preferably employed, especially synthetic polymers, with particular preference to be given to elastomeric polymers. It is also advantageous to employ transparent materials to manufacture the first layer adhering to the skin and/or the second covering or supporting layer, in that transparent electrodes allow examination of the surface of the skin situated beneath them.

The electrodes manufactured by the process of the invention may contain one or more sensors and are preferably round or square in shape. However, the electrodes may also be produced in any other desired shapes. The process of the instant invention can be employed for the manufacture of the electrodes described in the copending application entitled "Body Electrode," Ser. No. 411,375 filed concurrently herewith and incorporated herein by reference.

Any known natural or synthetic material which is elastic, mild to the skin, non-toxic, hydrophilic and which adheres to the skin may be used to manufacture the layer adhering to the skin. A prerequisite for this material is that it must be possible to cast it in any shape. The material in question preferably comprises a synthetic, preferably elastomeric, polymer or a mixture of polymers and/or a collagen. This material is either intrinsically conductive or rendered conductive by addition of an electrolyte. Preferably, synthetic organic polymers or polymer mixtures which are either intrinsically conductive or rendered conductive by addition of an electrolyte are used to manufacture the first layer adhering to the skin. These polymers must be castable in the form of a solution, a melt, or a corresponding low-viscosity prepolymer. A wide selection of polymers meeting these requirements is available. Suitable conducting polymers are, for example, the polymers described in U.S. Pat. No. 4,066,078, consisting of 2-acrylamido-2-methylpropane sulfonic acid, its salts, copolymers of the salt in question, copolymers of the salts of the acid, and mixtures thereof with water, alcohols, and water-alcohol mixtures; the polymers described in DE-OS 29 35 238 containing at least 5 mole percent monomer units containing a salt of a carboxylic acid; and also the conducting polymer compounds, which consist of a hydrophilic crosslinked polymer and a hydrophilic non-crosslinked polymer and which are described in EP 85 237.

Polymers which are not intrinsically conductive and are rendered such by addition of an electrolyte include, among others, polyvinyl alcohols, polyvinyl acetates, polyvinyl propionates and polyvinyl ethers, for example, as described in *Adhesion* 5/81, pages 208-213, as well as polyacrylates and polymethacrylates, such as those described in DE-OS 31 36 366, U.S. Pat. No. 4,554,924, and DE-AS 28 14 061.

The unsaturated acrylate resin types marketed by BASF under the trademark LAROMER. most preferably the resin marketed under the trademark LA- ROMER EA-8812 TM, have been found to be especially well suited.

To increase or control the adhesiveness, these polymers may additionally contain one or more tackifying agents, such as the glycidyl ether acrylates and their derivatives, which are known to be suitable for this purpose. They may also contain plasticizers (softeners) and/or hygroscopic agents, i.e., polyols such as diols and triols, for example, hexane triols, polyethylene glycol, etc. It is also advisable that the polymers contain added bacteriostatics and odor absorbents such as eucalyptol.

As has already been noted, the polymers employed to manufacture the first layer coming into contact with the skin are cast in a mold in a castable state, either in the form of a solution, a melt, or a prepolymer hardenable by crosslinking. The latter embodiment is preferred. The hardening is preferably accomplished by irradiation with ultraviolet light and/or heat using known photoinitiators and/or hardening accelerators. Examples of suitable compounds include per compounds such as peroxides and/or ketone hardening accelerators, such as for example, 2-hydroxy-2-methyl-1-phenylpropan-1-one, which is an effective photoinitiator for acrylated epoxies, acrylated polyurethanes, acrylated polyethers, and acrylated unsaturated polyesters or mixtures thereof.

The adhesion, conductivity, and elastic properties of the layer coming in contact with the skin can be customized by varying the type and amount of the conductive polymers employed, either ones naturally conductive or ones rendered conductive by addition of an electrolyte, and of any tackifying agent, plasticizer and/or hygroscopic agent employed, and also of the degree of cross-linking and hardening.

Preferably alkali halides such as potassium chloride are employed as electrolytes to render non-conducting polymers conductive for manufacture of the first layer coming in contact with the skin.

The material used to manufacture the second layer, i.e., the covering or supporting layer, may be any natural and/or synthetic hydrophilic material, in particular a polymer, which is also castable in the form of a solution, a melt, or a cross-linkable or hardenable prepolymer and which combines with the material of the first layer, i.e., the layer coming in contact with the skin, during solidification. The material for the covering second layer must of course not be conductive and must also contain no additives rendering it conductive As with the first layer, the second layer may be transparent as well. The many known materials meeting the specified requirements include, among others, polymers, especially elastomeric polymers, gelatins, especially ossein, with a gelatin strength of 60 to 200 Bloom and a cast gelating Shore hardness of 40 to 90 Shore, as well as in particular the polyacrylates which are employed to produce the covering second layer but which are both cross-linked and hardened so that they are no longer adhesive. Hence, in accordance with the invention, preference is to be given in the manufacture of the covering second layer to the use of the same polyacrylate prepolymers employed in manufacture of the first layer coming in contact with the skin, but which are cross-linked or hardened to a greater extent so that they are no longer adhesive. This results in especially strong bonding of the polymers of the first layer coming in contact with the skin and the covering second layer.

The layer adhering to the skin and the covering second layer may consist of the same material, in which case the layer adhering to the skin must of course be made conductive by addition of an electrolyte, as well as adhesive. The adhesiveness can be achieved by addition of a tackifying agent, in the event that cross-linkable polymers are used to produce the two layers, by making the layer coming in contact with the skin less cross-linked than the covering layer, in the event that less heavily cross-linked polymers are sufficiently adhesive.

In a preferred embodiment of the process of the present invention, a layer, preferably a transparent layer, bearing symbols is inserted between the first and second layers, if either the first layer adhering to the skin and/or the second covering or supporting layer, especially the latter, consists of a transparent material. The symbols consist, for example, of captions or graphic images, in order to identify the electrode as to origin or application.

The material which may be used to produce the intermediate layer provided with symbols may also comprise a castable natural or synthetic material. The same materials may be employed as are used to produce the layers coming in contact with the skin and the covering layers. However, the intermediate layer must not be electrically conductive.

The sensors employed in the body electrodes which are produced by the process of the invention are more or less known and are also described in the above-identified copending application.

The electrodes produced in accordance with the invention may also be identified by imprinting symbols or captions (such as company origin data or type designations) in the casting mold in reflected face type, whereupon the covering or supporting layer is cast first. The top of the electrodes produced in this manner are then provided on the second covering or supporting layer, with the raised symbols that have been formed.

The invention is described as follows with reference to synthetic elastomeric polymer materials used to produce the first layer adhering to the skin and the second covering or supporting layer of an electrode. The electrodes comprise a layer coming in contact with the skin (first layer), a plate-like sensor and a covering or supporting layer (second layer). The plate-like sensor contains a connection point for an electric lead, and its surface is smaller than the surface of the first layer. The second layer covers the side of the sensor facing away from the body and the first layer.

As has already been pointed out, the process of the invention can be applied by producing a melt of the polymers used to form the first layer adhering to the skin and by introducing these melts continuously with a metering hopper into a mold corresponding to the size and shape of the layer adhering to the skin, in an amount such that the desired layer thickness is achieved. After the melt has cooled or solidified at least to such an extent that the sensor when mounted does not penetrate too deeply into the first layer adheres to the skin, the sensor(s) is/are mounted on the layer produced, after which the second covering or supporting layer is cast in the desired thickness from a downstream metering hopper.

It is also possible to employ a solution of a polymer in a suitable solvent to cast the first layer adhering to the skin. After the layer has been cast, the solvent is evaporated, if necessary, at a faster pace by heating, and the polymer is cross-linked to the extent that the sensor which is mounted does not penetrate the formed layer to an undesirable depth.

This cross-linking or hardening can be accomplished by a known method with heat, light, ionizing radiation, or by using catalysts or initiators or hardening and polymerization accelerators. Combinations of these measures may also be applied, the measures applied being based on the type of polymer material employed.

Catalysts, initiators, or hardening or acceleration promoters are added to the casting solution appropriately immediately prior to the casting.

An additional method is also suitable for the present invention. In this method, a cross-linkable or hardenable preliminary stage of the elastomeric polymer to be employed is cast in a castable state. After the casting, cross-linking or hardening is carried out prior to application of the sensor at least to the extent that the cast layer is no longer so soft that the sensor can penetrate too deeply.

The covering or supporting layer is also cast by one of the three methods described above, but the method followed in any given instance must not be identical to the method by which the layer adhering to the skin is cast.

It is especially suitable, however, to use the same cross-linkable or hardenable preliminary polymer stage to produce both the layer adhering to the skin and the covering or supporting layer, the covering or supporting layer, which must no longer be adhesive, being more strongly cross-linked by one or more of the measures named than the layer adhering to the skin, which must remain adhesive. Cross-linking may be carried out in the manner described above.

The casting mold used to apply the process is preferably produced by deep-drawing sheeting of the desired shape and depth. Hence, for the purpose of industrial production molds situated side by side and one after the other are produced by deep-drawing from a strip of a material that does not combine with the material of the first layer adhering to the skin but can be detached from the first layer rather easily and without leaving residues. These molds are then brought in succession under metering devices for the purpose of feeding the castable material for the layer adhering to the skin, application of the sensors, and feeding of the castable material for the covering or supporting layer at the speed at which the devices in question operate. The metering devices in question may be installed downstream from irradiation or heating devices by means of which the crosslinking or hardening reactions can be carried out or accelerated.

The materials for the strip from which the molds for casting the body electrode of the invention are deep-drawn and preferably comprise a water-repellent polymer or polymer having a coating of an anti-adhesive or release agent such as a water-repellent silicone. Metal foils such as aluminum foils are also suitable.

It is suitable for the mold in which the body electrode has been produced by casting in accordance with the invention to be used as a protective layer so as to protect the layer adhering to the skin from damage or drying out. In this case, the electrode is marketed as a unit with the mold employed to produce it.

A variant of the process of the present invention comprises casting and hardening the layer adhering to the skin in a casting mold, introducing a sensor with electric connection capability, and then casting the covering or supporting layer with the sensor embedded.

Another variant of the process of the invention comprises introducing into a casting mold sheeting on all or part of which a galvanically active layer has been deposited, if desired, in specific configurations, for example, by a screen printing process. The layer adhering to the skin is cast on this sheeting in contact with the galvanically active layer, and a cover sheet is placed over it after solidification has taken place.

In the event of the manufacture of such a body electrode, the galvanically active layer may be connected to a recording instrument by introducing into the mold connecting leads which either project from the side prior to casting of the layer adhering to the skin or project upward from it. These leads may then be connected to lines leading to a recording instrument or instruments.

Like the galvanically active layer, however, the leads may also be applied in the form of a layer to the sheeting to be introduced into the casting mold, preferably in a thickness of 30 $\mu$m to 200 $\mu$m, it being advisable for them to end in a tab on the electrode, from which point they can then be connected to the recording instrument by means of a conventional electric cord.

In the event of the manufacture of an electrode from a layer coming in contact with the skin, a plate-like sensor, and a covering layer, the thickness of the first layer coming in contact with the skin preferably ranges from 800 $\mu$m to 2,500 $\mu$m, and with special preference from 1,000 $\mu$m and 2,000 $\mu$m, while the thickness of the covering second layer preferably ranges from 500 $\mu$m to 2,500 $\mu$m, and especially between 1,000 $\mu$m and 2,000 $\mu$m.

The thickness of the electrode plate of the plate-like electrodes employed in these electrode units ranges preferably from 50 $\mu$m to 1,500 $\mu$m, and especially from 80 $\mu$m to 1,000 $\mu$m. Such electrodes are preferably round and preferably have a diameter of between 20 mm and 60 mm.

The following example illustrates the invention:

A mixture of 100 g 1-vinyl-2-pyrrolidone, 10 g hydrogen peroxide (3% by weight solution in water), 7 g 4-(hydroxyethoxy)phenyl-(2-hydroxy-2-propyl)-ketone, 5 g polyetheracrylate, 15 g polyvinylpyrrolidone, 100 g propanetriol, 20 g distilled water, 4 g triethanolamine, and 5 g ammonium hydroxide (10% in water) was produced. 40 g of a solution of 30 g potassium chloride and 5 g sodium tetraborate in 100 g water were added to this mixture.

The layers coming in contact with the skin, of a thickness of 500 $\mu$m, were cast from the mixture obtained in deep-drawn round molds of silicone-coated polyethylene with a diameter of 50 mm and a depth of 3 mm. The cast layers were heated for a period of 15 seconds with ultraviolet light to a temperature of 60° C. A round plate-like sensor having a diameter of 6 mm and a sensor plate thickness of 1 mm was then applied to this layer.

Then a transparent mixture of 60 g propanediol, 5 g glycide etheracrylate, 40 g tripropyleneglycol diacrylate, 60 g polyethylene glycol-300, and 3 g 2-hydroxy-2-methyl-1-phenylpropan-1-one was cast as covering layer, in a thickness of 800 $\mu$m, on the structure obtained and was hardened for a period of 15 seconds at a temperature of 60° C. by the action of ultraviolet light. The body electrode thereby obtained was transparent on the places not covered by the sensor plate and adhered well to human skin without exerting any irritating effect.

What is claimed is:

1. A process for manufacturing a body electrode which comprises at least one galvanically active sensor, at least part of which is exposed through said electrode, a first layer on the body contact side of said sensors capable of adhering to the skin and comprising an electrically conductive, adhesive, elastic hydrophilic material, and a second layer on the side opposite the body contact side being a covering or supporting layer and comprising an elastic, non-adhesive material, said process comprising:

(a) casting a layer of said electrically conductive, adhesive, elastic hydrophilic material;
   (b) solidifying the material of step (a) to form said first layer on said body contact side of said electrode;
   (c) placing said galvanically active sensor or lead wires connected to a sensor on said first layer;
   (d) casting a layer of said elastic, non-adhesive material; and
   (e) solidifying the material of step (d) to form said second layer of said electrode,
   (f) wherein said solidifying is effective to bond the layer resulting from step (e) to the layer resulting from step (b).

2. The process of claim 1, wherein a melt, solution, or a cross-linkable or hardenable preliminary stage of the material to be cast is used for casting the first layer.

3. The process of claim 1, wherein the materials employed are selected from the group consisting of collagens, synthetic polymers, monomers and combinations thereof.

4. The process of claim 2, wherein the materials employed are selected from the group consisting of collagens, synthetic polymers, monomers and combinations thereof.

5. The process of claim 3, wherein said materials are synthetic polymers.

6. The process of claim 4, wherein said materials are synthetic polymers.

7. The process of claim 1, wherein the material employed for casting the first layer is transparent.

8. The process of claim 2, wherein the material employed for casting the second layer is transparent.

9. The process of claim 7, wherein the material employed for casting the second layer is transparent.

10. The process of claim 1, wherein molded sheeting is used as the casting mold.

11. The process of claim 1, wherein the body electrode comprises a third intermediate layer, the first layer is transparent, and the third layer is provided with symbols and is inserted between the first and second layers.

12. The process of claim 11, wherein the body electrode comprises a third intermediate layer, the second layer is transparent, and the third layer is provided with symbols and is inserted between the first and second layers.

13. The process of claim 12, wherein the material employed for casting the second layer is transparent.

14. The process of claim 11, wherein said third layer is transparent.

15. The process of claim 12, wherein said third layer is transparent.

16. The process of claim 13, wherein said third layer is transparent.

17. A process for manufacturing a body electrode which comprises at least one galvanically active sensor, at least part of which is exposed through said electrode, a first layer on the body contact side of said sensors capable of adhering to the skin and comprising an electrically conductive, adhesive, elastic hydrophilic material, and a second layer on the side opposite the body contact side being a covering or supporting layer and comprising an elastic, non-adhesive material, said process comprising:

(a) casting a layer of said elastic, non-adhesive material;
   (b) solidifying the material of step (a) to form said second layer of said electrode;
   (c) placing said galvanically active sensor, or lead wires connected to a sensor, on said second layer;
   (d) casting a layer of said electrically conductive, adhesive, elastic hydrophilic material; and
   (e) solidifying the material of step (d) to form said first layer of said electrode;
   wherein said solidifying is effective to bond the layer resulting from step (e) to the layer resulting from step (b).

18. The process of claim 17, wherein a melt, solution, or a cross-linkable or hardenable preliminary stage of the material to be cast is used for casting the first layer.

19. The process of claim 17, wherein the materials employed are selected from the group consisting of collagens, synthetic polymers, monomers and combinations thereof.

20. The process of claim 19, wherein the materials employed are selected from the group consisting of collagens, synthetic polymers, monomers and combinations thereof.

21. The process of claim 19, wherein said materials are polymers.

22. The process of claim 20, wherein said materials are polymers.

23. The process of claim 17, wherein the material employed for casting the first layer is transparent.

24. The process of claim 18, wherein the material employed for casting the second layer is transparent.

25. The process of claim 18, wherein molded sheeting is used as the casting mold.

26. The process of claim 18, wherein the body electrode comprises a third intermediate layer, the first layer is transparent, and the third layer is provided with symbols and is inserted between the first and second layers.

27. The process of claim 26, wherein the body electrode comprises a third intermediate layer, the second layer is transparent, and the third layer is provided with symbols and is inserted between the first and second layers.

28. The process of claim 27, wherein the material employed for casting the second layer is transparent.

29. The process of claim 24, wherein said third layer is transparent.

30. The process of claim 27, wherein said third layer is transparent.

31. The process of claim 28, wherein said third layer is transparent.

* * * * *